United States Patent [19]
Takagi et al.

[11] Patent Number: 5,531,794
[45] Date of Patent: Jul. 2, 1996

[54] CERAMIC DEVICE PROVIDING AN ENVIRONMENT FOR THE PROMOTION AND FORMATION OF NEW BONE

[75] Inventors: Shigehide Takagi, Tokyo; Kuniomi Ito, Tochigi-ken; Tsuneo Hidaka, Tokyo, all of Japan

[73] Assignee: Asahi Kogaku Kogyo Kabushiki Kaisha, Tokyo, Japan

[21] Appl. No.: 305,440

[22] Filed: Sep. 13, 1994

[30] Foreign Application Priority Data

Sep. 13, 1993 [JP] Japan .................................. 5-227127

[51] Int. Cl.⁶ .................................................. A61F 2/28
[52] U.S. Cl. ............................. 623/16; 433/2011; 606/76
[58] Field of Search ........................... 623/16; 433/201.1; 606/76

[56] References Cited

U.S. PATENT DOCUMENTS

| | | |
|---|---|---|
| 4,113,500 | 9/1978 | Ebihara et al. . |
| 4,149,894 | 4/1979 | Ebihara et al. . |
| 4,629,464 | 12/1986 | Takata et al. ............................. 623/16 |
| 4,897,250 | 1/1990 | Sumita . |
| 4,919,751 | 4/1990 | Sumita et al. . |
| 4,957,674 | 9/1990 | Ichitsuka et al. . |
| 4,960,426 | 10/1990 | Atsumi ...................................... 623/16 |
| 5,017,518 | 5/1991 | Hirayama et al. . |
| 5,064,436 | 11/1991 | Ogiso et al. . |
| 5,089,195 | 2/1992 | Ichitsuka et al. . |
| 5,141,510 | 8/1992 | Takagi et al. ............................ 623/16 |
| 5,171,720 | 12/1992 | Kawakami . |
| 5,215,941 | 6/1993 | Yasukawa . |
| 5,263,985 | 11/1993 | Bao et al. .................................. 623/16 |
| 5,310,548 | 5/1994 | Tsuru et al. . |

FOREIGN PATENT DOCUMENTS 63-319048 12/1988 Japan .

*Primary Examiner*—Paul B. Prebilic
*Attorney, Agent, or Firm*—Greenblum & Bernstein

[57] ABSTRACT

A ceramic device providing an environment for the promotion and formation of new bone. The ceramic device is made of a sinter of calcium phosphate compound, containing a plurality of perfect spherical pores whose diameter ranges from 10–450 µm to provide a suitable environment for the formation of new bone. A plurality of micro pores is included whose diameter ranges from 0.01–0.5 µm which surrounds the perfect spherical pores to interconnect the perfect spherical pores with an outer surface of the ceramic device with the micro pores interconnecting with each other.

6 Claims, 4 Drawing Sheets

CERAMIC DEVICE PROVIDING AN ENVIRONMENT FOR THE PROMOTION AND FORMATION OF NEW BONE

BACKGROUND OF THE INVENTION

1. Field of the Invention

The present invention relates to a ceramic device which is made of a sinter of calcium phosphate compound, having an excellent bio-compatibility to provide an environment for the promotion and formation of new bone mass (material).

2. Description of Related Art

Artificial elements have been implanted to recover the function of hard tissue or soft tissue of a living organism. Such implant materials that are known include metals, plastics, ceramics and composite ceramics. One of the most significant requirements for the implant material is to be bio-compatible with the receiver. From this view point, ceramic materials are considered ideal because ceramic is less harmful and more stable than other materials. Among the group of ceramic materials, it has been found that calcium phosphate compounds have a composition similar to the hard tissue of living organisms and accordingly, have been identified to be optimum implant materials. Indeed, calcium phosphate compounds have been used as artificial bones, and particularly, as a prosthesis for missing parts of bone.

In the case where a porous calcium phosphate compound is used to replace a missing segment of a bone, it is chosen due to its porous nature and that it bonds well with the natural bone. It has been observed that part of the natural bone grows into and is absorbed by the pores of the calcium phosphate compound, which becomes part of the new living bone structure. Consequently, porous calcium phosphate compound ceramics have been widely used as implant materials.

Nevertheless, there is no substantial analysis or study of a correlation between the form of the pores that constitute the porous material and the formation of the bone. Even for porous implant materials which are available in the market place, the above-mentioned correlation has not been taken into account when designing or administering these materials. For instance, if a pore which should be connected with an outer surface of the material is covered, no transport of body fluids within the implant material can be established and therefore, little new bone mass is formed within the pore. Consequently, the implant material remains inactive, leading to an inadequate bond being formed between the implant material and the surrounding living bone. In this case, the implant material is identified as foreign matter and is rejected by the living body. Furthermore, if there are a large number of pores through which living cells and body fluids can flow, then the formation of new bone mass within the pore requires much more time due to a free movement of the macro-phage, macro foreign cells within the implant material. Therefore, the implant material cannot satisfactorily achieve the proper function thereof due to lack of calcification. As can be seen from the foregoing, the pores are very important factors in determining the quality of the new bone structure. Nevertheless, conventional porous implanting materials have not been sufficiently studied from a scientific or functional view point.

SUMMARY OF THE INVENTION

It is an object of the present invention to eliminate the above-mentioned drawbacks by providing a porous ceramic device in which the shape or form of the pores are designed so as to have excellent properties for use as an implant material, thereby providing an environment for the promotion and formation of new bone mass.

Another object of the present invention is to provide a method for producing such a porous ceramic device.

The inventors of the present invention have found that a porous calcium phosphate compound sinter including a plurality of perfect spherical pores having a specific diameter and a plurality of micro pores (smaller pores) of a specific diameter, (that are provided to surround the perfect spherical pores to connect the pores to the outer surface of the material and that interconnect with each other) can achieve the object mentioned above.

To achieve the object, according to the present invention, a ceramic device is provided including an environment for the promotion and formation of new bone mass. The ceramic device is made of a sinter of calcium phosphate compound, containing a plurality of perfect spherical pores whose diameter is in the range 10–450 µm to provide the environment for the formation of new bone mass. Also included are a plurality of micro pores whose diameter is in the range 0.01–0.5 µm, surrounding the perfect spherical pores to connect the perfect spherical pores and an outer surface of the ceramic device, the micro pores interconnecting with each other.

The ceramic device is made of a sinter of calcium phosphate compound. A calcium phosphate compound can be used in the form of $CaHPO_4$, $Ca_3(PO_4)_2$, $Ca_{10}(PO_4)_6(OH)_2$, etc., solely or in combination. For hydroxyapatite, a part or entirety of Ca, $PO_4$, and OH can be replaced with similar chemical elements or atomic groups from the group of hydroxyapatite.

The ceramic device according to the present invention includes a plurality of perfect spherical pores having a diameter in the range 10–450 µm and a plurality of micro pores in the range 0.01–0.5 µm surrounding the same, within the calcium phosphate compound sinter, as mentioned above. The perfect spherical pores whose diameter in the range 10–450 u m provide not only an environment to cause cells to form new bone mass, but also an environment in which osteogenic cells are created due to the free flow of blood plasma within the new bone formation site.

If the diameter of the perfect spherical pores is below 10 µm, the creation of osteogenic cells is slowed, thus resulting in a retardation of the formation and growth of a bone. Conversely, if the diameter is above 450 µm, it is impossible for the cells to be absorbed into the walls of the perfect spherical pores within a short period of time, thereby allowing the cells to generate and grow blood vessels. In general, in such a porous structure where the diameter of the pores is above 450 µm, there is a possibility that the strength of the implant device is reduced. Further, it is preferable that the pores are as close to perfect spheres as possible and are uniformly distributed throughout the implant material. The term "perfect spherical pore(s)" referred to in this specification includes substantially perfect spherical pore(s). The aspherical shape also contributes to an appropriate distribution of an external stress applied to the implant material without concentrating the stress, in addition to allowing an accelerated formation of new bone mass.

The micro pores communicating with each other and surrounding the perfect spherical pores to connect the same to the outer surface of the implant device can be adapted as a filter which permits only body fluids, blood plasma components or new bone forming cells (e.g., osteoblasts, osteocytes, etc.) to pass through, thereby promoting the activation of new cells to form within the perfect spherical pores, and to help form new bone mass. Hence, the micro pores fulfill a function as a factory for generating new cells. In theory, the micro pores can be dispensed with since the perfect spherical pores make it possible for the osteogenic cells, body fluids, and blood plasma components to travel. However, in the absence of micro pores, if a large number of osteogenic cells within the perfect spherical pores are grown to form an osteone structure, the perfect spherical pores could fill, resulting in a loss of supply of nutrition from the outer surface to the new bone mass forming site. Therefore, the micro pores are useful in that they provide special passages for nutrition to be supplied to the cells and for the transfer of the substances to and away from the new bone mass forming site when there is a large number of osteogenic cells blocking the perfect spherical pores, thus preventing direct connection with the outer surface. To this end, the size of the micro pores is such that no cells can enter the micro pores to close the passages. The upper and lower limits (0.01 µm, 0.5 µm) mentioned above are derived from the requirements previously discussed. If the size of the micro pores is below 0.01 µm, it is difficult for the body fluids or blood plasma to flow. Conversely, if the size of the micro pores exceeds 0.5 µm, there is a possibility that monocytes or other cells may enter the micro pores.

The ceramic device as constructed above, which has an improved bone forming function can be of any shape including granular, cubic, parallelepiped, cylindrical or disc shaped. Moreover, the size of the ceramic device is not limited to a specific value. If the ceramic device is made of a relatively large block (e.g., 3×3×3 cm$^3$ or 5×5×5 cm$^3$), it takes a long time before the formation of new bone mass takes place at the center portion thereof. In an extreme case, the formation of the bone occurs only at the outer surface portion of the implant element, so that no cells can enter the central portion of the block to form new bone mass.

In view of this, in the case of a relatively large implant device, the implant device is preferably provided with at least one tubular passage to connect a pair of opposed surfaces of the implant device. If the implant device is orientated in the direction of the blood flow of the defective portion of the living body, then the growing and hyperplasia of regenerated blood vessels within the pores can be carried out at the center portion of the implant device. In this manner, not only can the blood flow be obtained at the center portion, but the osteogenic cells can be fully supplied with nutrition. The tubular passages are intended to transport the osteogenic cells, body fluids and blood plasma to the center portion of the implant device. Each tubular passage preferably has a diameter of 0.6–1.2 mm. If the diameter is smaller than 0.6 mm, it is difficult for the blood and blood components to smoothly flow to the new bone formation site. Conversely, if the diameter of the tubular passage is larger than 1.2 mm, the strength of the whole implanting device can be adversely compromised.

If there is more than one tubular passage, they are preferably spaced at a distance of 3–5 mm apart in cross section of the implant device, perpendicular to the direction of the tubular passages. If the distance is below 3 mm, the strength of the implant device can be adversely compromised, whereas if the distance is above 5 mm, an insufficient supply of the osteogenic cells or nutrition can occur.

From the view point of the formation of new bone mass, it is preferable that there are many tubular passages at a small distance apart, whereas, from the view point of the strength of the implant device, it is preferable that there are few tubular passages and which would be far apart. To ensure an effective formation of new bone mass with the least number of tubular passages possible, it is preferable that there are a plurality of tubular passages, including one center passage located at the center of a circle and peripheral passages that are located on the circle at an equi-angular distance, i.e., in a cross section perpendicular to the length of the cylinder. With this preferable arrangement, a distance between any adjacent tubular passages can be equal to or less than 5 mm.

The following discussion will address a method for the production of a ceramic implant device according to the present invention.

According to another aspect of the present invention, a method is provided for producing a ceramic device providing for the promotion and formation of a bone, comprising the steps of: preparing a molded product containing pores or a thermally vanishing (e.g., sublimating) spherical substance from spherical particles of calcium phosphate compound having a 5–10 µm particle size; and, preparing a porous sinter by calcining the molded product obtained. The porous sinter contains a plurality of perfect spherical pores of a 10–450 µm diameter and a plurality of micro pores whose diameter is 0.01–0.5 µm, which surround the perfect spherical pores to connect the same and an outer surface of the ceramic device, with the micro pores communicating with each other.

As can be understood from the above discussion, according to the present invention, an implant ceramic device which has a good biocompatibility and an optimum porous structure from the view point of promoting new bone mass regeneration and calcification, can be obtained. The perfect spherical pores of 10–450 µm diameters provide not only an environment for the formation of new bone mass, but also an environment for the activation and generation of osteogenic cells derived from the flow of blood plasma components. The micro pores, whose diameter is 0.01–0.5 µm, function as a filter to permit only the body fluids or the blood plasma products to pass through, so that the activation of the osteogenic cells residing in the perfect spherical pores can be accelerated.

Furthermore, according to the present invention, the tubular passages supply the implant tissue structure with cell components which are directly adapted to form a new bone mass without the interruption of the flow of necessary blood. The provision of the tubular passages is particularly advantageous for relatively large implant devices. If the implant device is implanted in the direction of the blood flow of the defective portion of the living body, not only can the growing and hyperplasia of regenerated blood vessels within the pores occur even at the center portion of the implant device, but also a blood flow can be ensured, resulting in a stable supply of new bone mass forming cells, nutrition, etc. Consequently, in comparison with the conventional device, the formation of bone can be effected in an extremely short space of time. Moreover, a stable growth of the regenerated bone can be expected for a long time. Finally, the regenerated new bone mass, together with the living bone, forms a biocomposite that can semi-permanently fulfill the function of natural bone.

To form an implant device having micro pores of 0.01–0.5 µm, a powder of calcium phosphate compound is granulated in advance to prepare spherical particles having a diameter of 5–10 micro meter (i.e., microns). In the production method according to the present invention, the spherical particles thus obtained are used as raw materials to form a molded product which is then calcined to produce a porous sinter. The molded product can be produced in either a dry method or wet method. In a dry method, for example, the raw material is mixed with a thermally vanishing perfect spherical substance of a range 12–700 μm in particle size. The mixture is then compressed and molded to obtain a green compact. A thermally varnishing substance which sublimes, such as naphthalene, adamantane, trimethylnorborane, p-dichlorobenzene, a mixture of adamantane and trimethylnorbornane, cyclododecane or synthetic resin such as polymethyl methacrylate, polypropylene, polystyrene, polyethylene, can be used. The particle size of the thermally vanishing substance is determined taking into account the shrinkage due to calcination in which pores are produced when the subliming substance vanishes upon calcining and the remaining material contracts. In general, it is said that a linear shrinkage of 60%–80% occurs.

In the wet method, a foamed slurry is prepared by: using a foaming agency such as hydrogen peroxide or albumen; casting; and heating and drying. This serves to form a molded product having a large number of pores.

Thereafter, the molded product is calcined, for example, in an electric furnace in which the temperature gradient is well controlled, taking into account the kind of calcium phosphate compound to be used or the diameter of the pores, etc., to thereby obtain a sinter having the desired arrangement of pores.

The functional ceramic material having at least one tubular passage with a diameter of 0.6–1.2 mm, that connects at least one pair of opposed surfaces of the material, can be produced in various methods.

Namely,

Method 1) The molded product obtained by the processes mentioned above is shaped into a desired shape having at least one pair of opposed surfaces. It is then machined to have at least one tubular passage connecting the opposed surfaces and then burnt or calcined:

Method 2) A green compact is made from the raw material mentioned above. The thermally vanishing spherical substance of 12–700 μm in particle size, and a thermally vanishing substance of which the tubular passages of 0.7 to 1.8 mm diameter are then calcined or burnt:

Method 3) A foamed slurry is prepared using a foaming agent and poured into a molding die with a flat bottom. Tubular passage forming members of a thermally vanishing substance having a 0.7–1.8 mm diameter and a length long enough to reach the bottom from the liquid surface are hung in the slurry; and calcined or burnt:

Method 4) A foamed slurry is prepared using a foaming agent and poured into a molding die which is provided on the bottom surface thereof with at least one tubular passage forming upright pins of 0.7–1.8 mm diameter which extend from the bottom surface to the liquid surface of the mold. The molded product is then dried and removed from the molding die; and is then burnt or calcined.

In any of the methods mentioned above, the selection of the temperature gradient upon burning is a very important factor to control the growth of the particles. Namely, the temperature gradient is controlled so that the gaps between the spherical particles correspond to the micro pores. The micro pores function as the filters mentioned above. The curvature of the perfect spherical pores produced by the foaming agent provides an environment for the osteogenic cells. Furthermore, the perfect spherical pores define a space in which the osteogenic cells reside. The tubular passages provide a blood vessel growing space.

The present disclosure relates to subject matter contained in Japanese patent application No. 5-227127 (filed on Sep. 13, 1993) which is expressly incorporated herein by reference in its entirety.

BRIEF DESCRIPTION OF THE DRAWINGS

The invention will be described below in detail with reference to the accompanying drawings, in which.

DESCRIPTION OF THE PREFERRED EMBODIMENT

Figure 1:
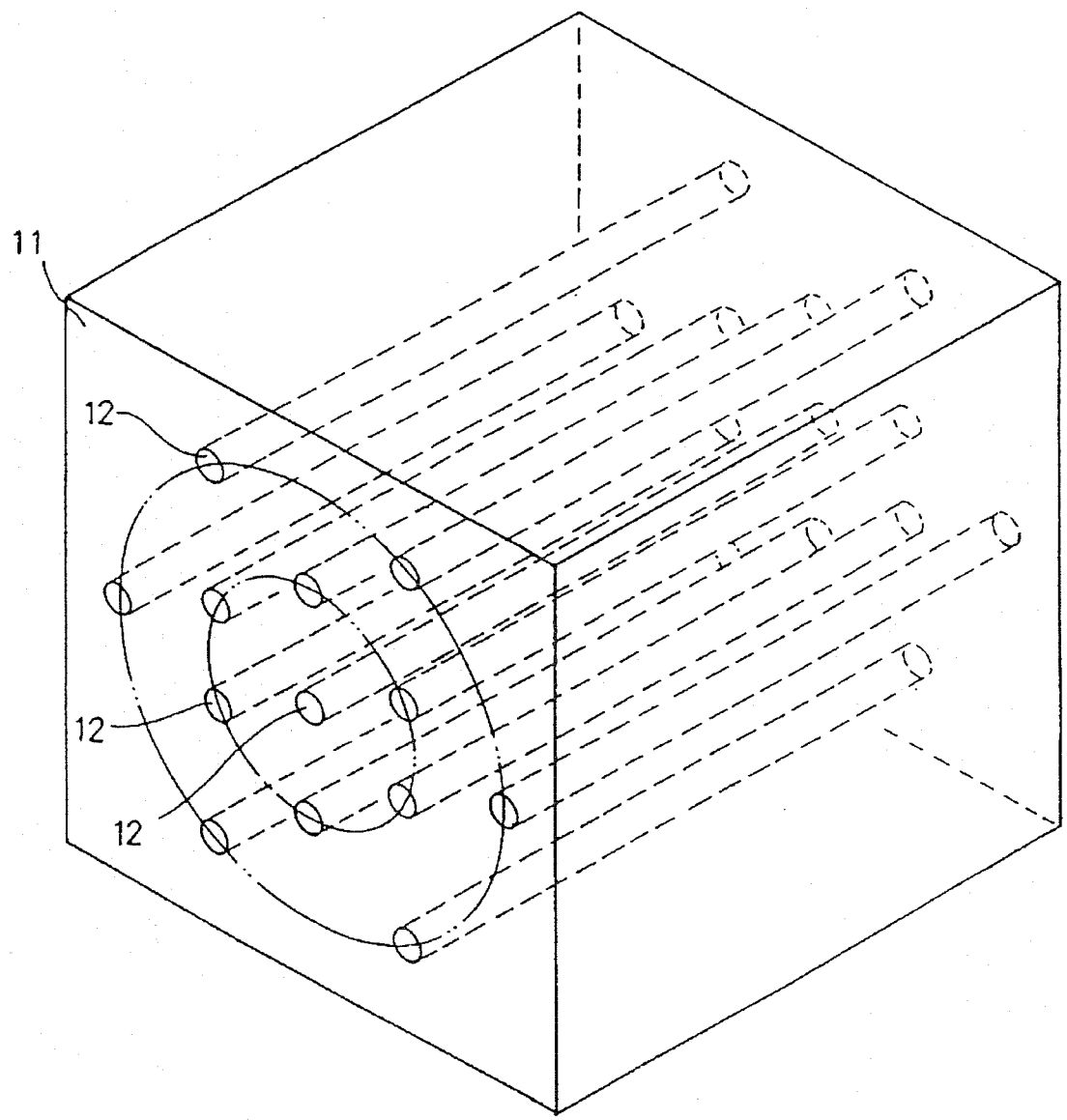
FIG. 1 is an isometric view of a rectangular shaped columnar implant device according to one aspect of the present invention.
Figure 2:
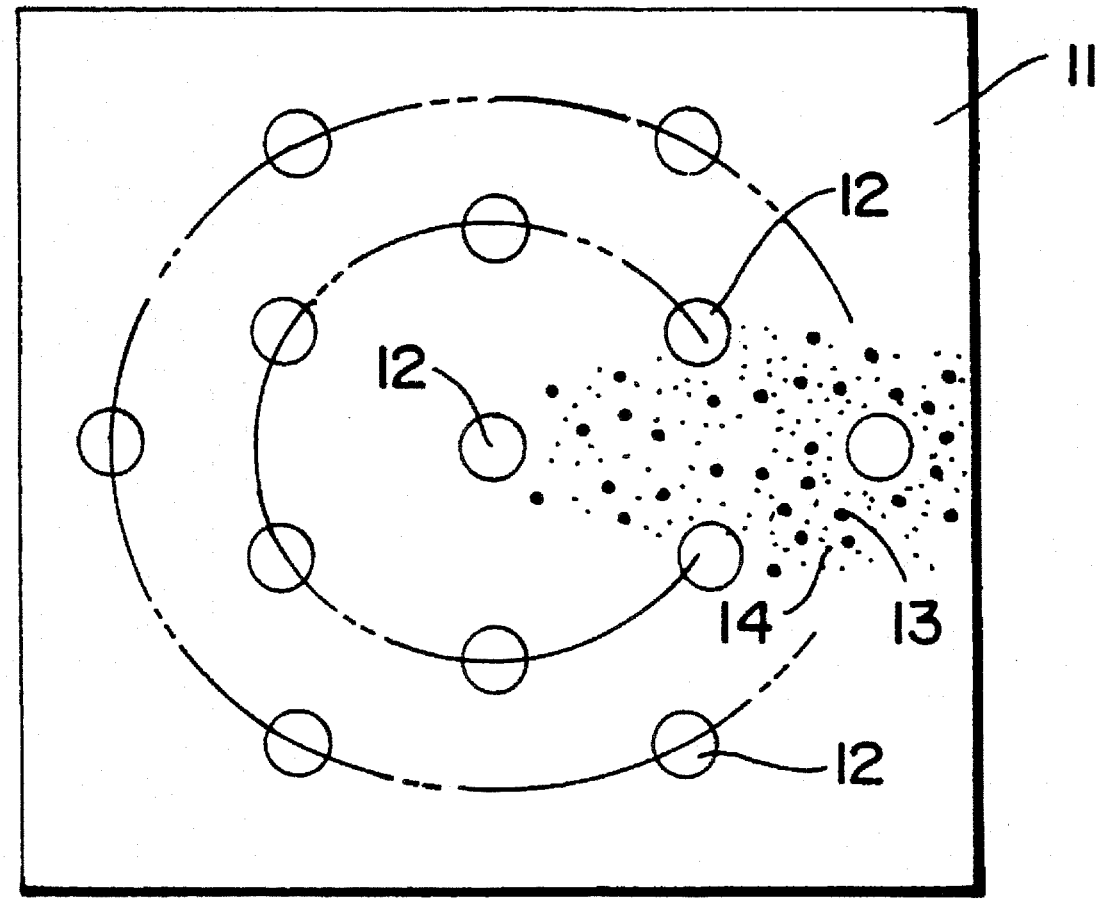
FIG. 2 is an explanatory sectional view of an implant device in FIG. 1.

FIGS. 1 and 2 show an example of an implant device according to the present invention.

As can be seen in FIGS. 1 and 2, an implant device 11 having a rectangular shaped column 11 is provided with tubular passages 12, extending in a direction parallel to the column. One tubular passage 12 is provided at the center of the column 11, and the remaining tubular passages 12 are arranged around the center tubular passage in a hexagonally symmetrical fashion.

Figure 3:
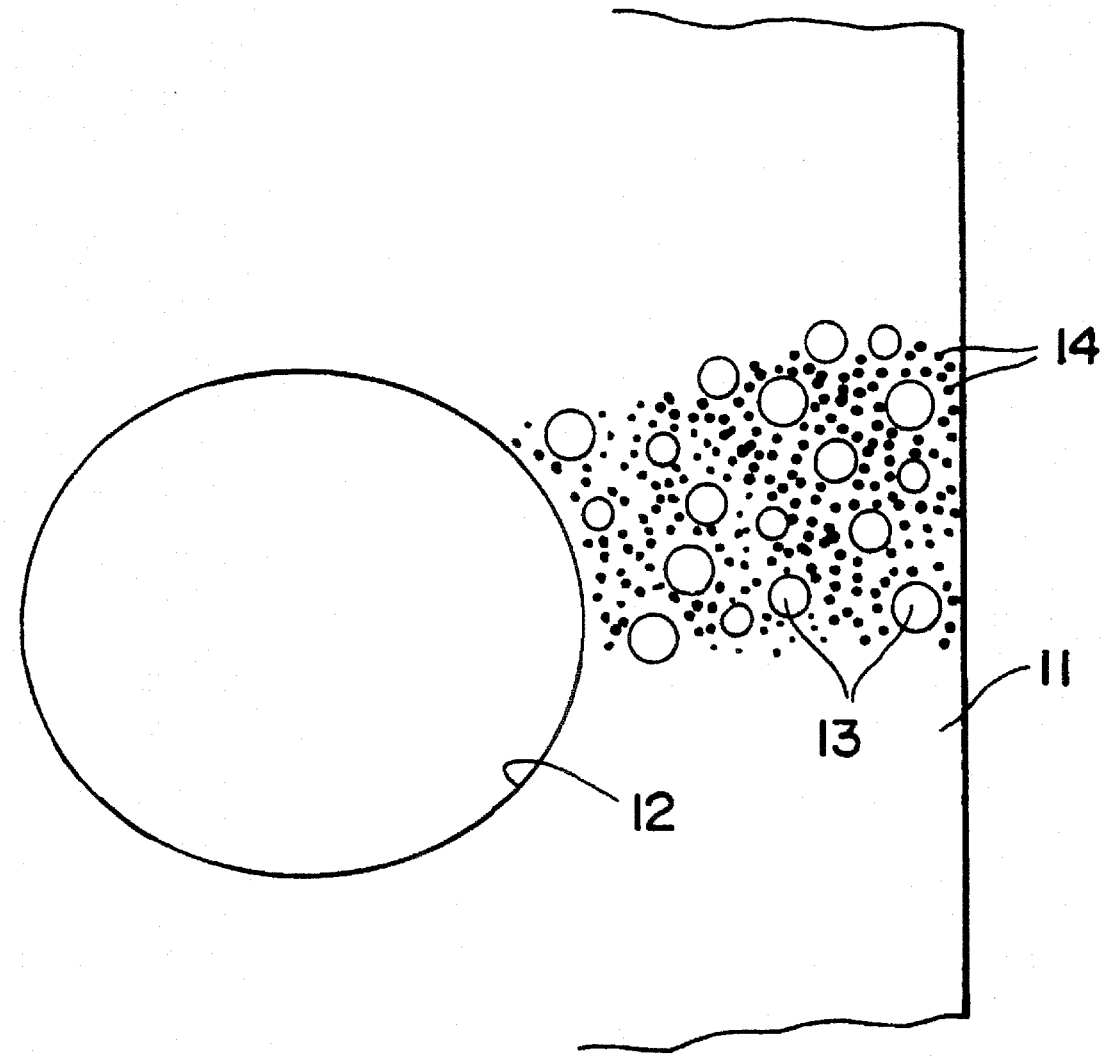
FIG. 3 is an enlarged explanatory sectional view of the implant device shown in FIG. 1.

In FIG. 3, a plurality of perfect spherical pores are designated by the numeral 13, and a plurality of micro pores are designated by the numeral 14. The micro pores 14 connect not only the pores 13 but interconnect to an outer surface of the implant device 11 and an inner surface of tubular passage 12.

Figure 4:
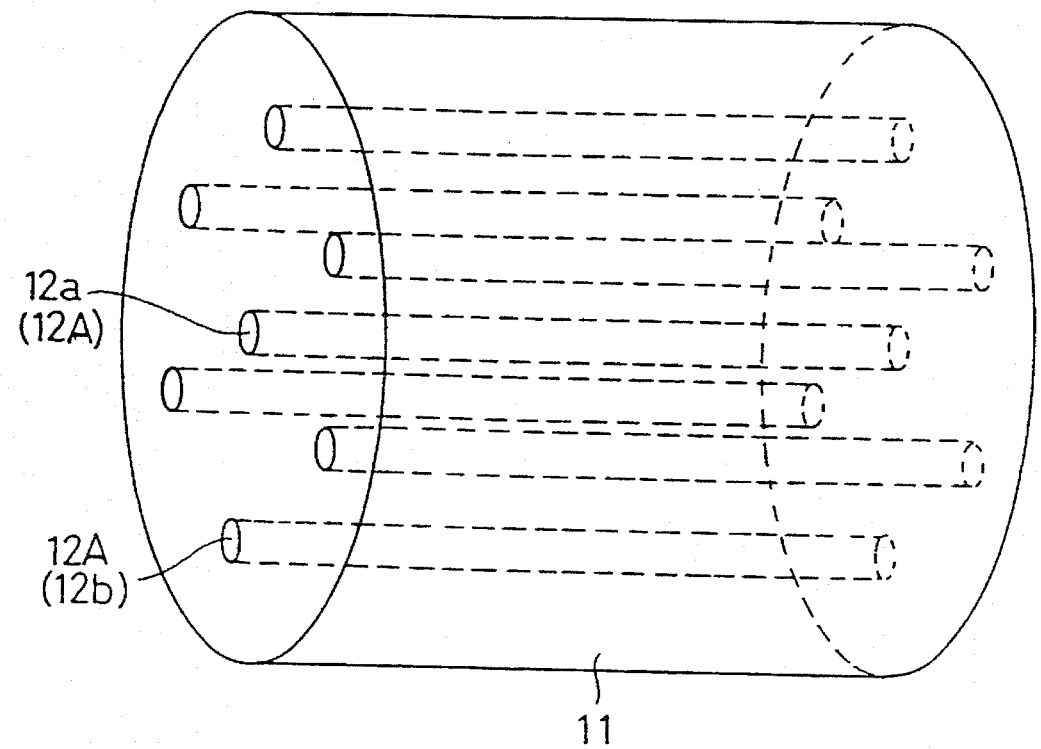
FIG. 4 is an isometric view of a cylindrical implant device according to another aspect of the present invention; and, FIG. 5 is an explanatory sectional view of the implant device shown in FIG. 4.
Figure 5:
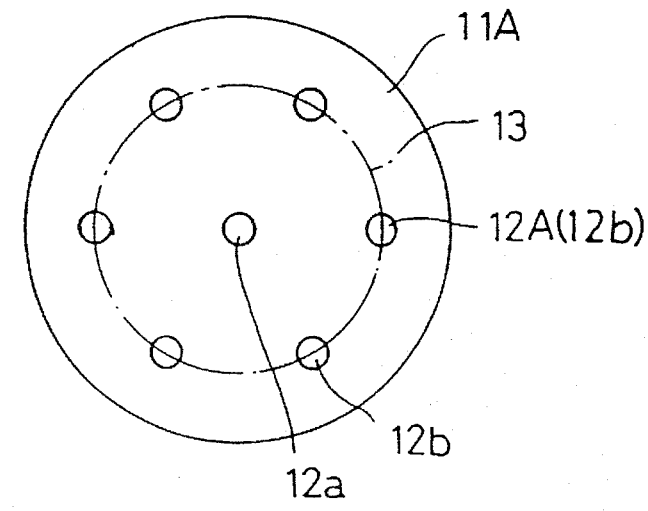

FIGS. 4 and 5 show an example of an implant device according to another embodiment of the present invention.

As can be seen in FIGS. 4 and 5, the cylindrical implant device 11A is provided with seven tubular passages 12A in total, extending in a direction parallel to the length of the cylinder. The tubular passages 12A are uniformly distributed, equi-distantly from each other. Namely, there is one central passage 12a located at the center of a circle defined by the configuration of the cylinder and six peripheral passages 12b that are located on the same phantom circle 13 at equi-angular positions. For example, the diameter of phantom circle 13 is around 1 cm, and is equi-distant from seven passages 12 at a distance of about 3–5 mm.

Several examples of the present invention will be described below. Note that the present invention is not limited to the examples.

EXAMPLE 1

Hydroxyapatite was synthesized in a known wet method per se, to obtain a hydroxyapatite slurry which was then sprayed and dried using a rotary spray-dryer to obtain a powder of spherical particles of hydroxyapatite having 5–9 μm particle size.

100 g of a powdered albumen was added to and slowly mixed with the 200 g of the powdered hydroxyapatite obtained, by a dry type ball mill. The average particle size of the powdered mixture was 6.5 μm. 500 g of water was added to the powdered mixture thus obtained and stirred for 15 minutes by a hand mixer. Thereafter, the mixture was transferred to a glass petri dish, whose depth and diameter were 5 cm and 20 cm, respectively, and dried for 24 hours in a dryer at 80° C. Thereafter, the dried mixture was cut into a cylindrical post having 1.2 cm diameter and 1 cm height. A through hole of 1.2 mm diameter was then formed in the central tubular passage connecting the opposed end surfaces of the cylindrical post. Moreover, six through holes were pierced to form the peripheral tubular passages spaced at an equi-distance of 4 mm. The cylindrical post was then calcined for two hours at 1100° C. in an electric furnace to obtain a ceramic implant device.

The size of the sinter obtained was such that the diameter and height of the cylindrical post were 8 mm and 7 mm, respectively. The distance and diameter of the tubular passages were 3 mm and 0.8 mm, respectively, as a result of the expected shrinkage during calcination. The average porous diameters of the micro pores and the perfect spherical pores that were measured by a mercury porosimeter were 0.3 μm and 350 μm (distribution having two peaks), respectively.

The implant devices produced were implanted in the marrow of a femur of an adult beagle dog and taken out as tissue samples two weeks and four weeks later to inspect the state of the bone formed within the structures of the implant tissues. For the former tissue (two weeks later), it was found that a lining cell structure was formed on the inner wall of the perfect spherical pores up to and including the center portion of the implant. This was considered to indicate new bone mass being formed as identified by dye imaging. On the other hand, for the latter tissue (four weeks later), it was confirmed that a large part of the perfect spherical pores were filled with new bone. Namely, a remarkable growth of the bone was found through imaging techniques, in comparison with a conventional structure having no micro pores.

EXAMPLE 2

The implant device produced in example 1 mentioned above was machined into two laminated circular discs having diameters of 15 mm and 12 mm, respectively. Both discs had the same thickness of 4 mm. The laminated discs were implanted in a missing part of a skull of an adult beagle dog (10 years old) which was formed by piercing the bone to thereby form a hole of 13 mm diameter at the side of the skull. The implantation was effected in such a way that the lower disc of 12 mm diameter was inserted in the pierced hole of 13 mm diameter. Consequently, there was an annular clearance of 0.5 mm between the inner wall of the pierced hole and the lower disc. In this state, the implant device was able to move when an external force was applied by a finger.

Thereafter, the implant device was held by the galeal layer and sutured. Three days later, there was no movement of the implant device even by the application of the external force by a finger through the scalp of the dog. This meant that the implant device was almost completely secured.

During an autopsy of the beagle dog three weeks later, it was found that the annular clearance between the implant device and the pierced hole of the skull was filled with a new bone and the suture was kept in place.

EXAMPLE 3

A piece of tibia of an adult beagle dog having a cross sectional area of ½ cm² and length of 15 mm was cut and removed from a lower portion of a tibial epiphyseal line. An implant device whose shape was similar to that of the removed piece was implanted in the missing portion of the tibia. The material of which the implant device was made was the same as in example 1 mentioned above. X-ray findings were obtained at three days, one week, three weeks, five weeks, seven weeks, nine weeks, 12 weeks, 26 weeks and 52 weeks after the operation. In parallel with the X-ray findings, biochemical examinations of the blood of the dog were conducted. The changes occurring at the boundary portion of the implant device and the associated new bone mass, as well as the formation of the new bone, were mainly observed through the X-ray images. As a result, images showing the prosperous formation of a bone were found at 5–9 weeks. It was also found through the biochemical examinations of the blood that a high alkaline phosphate level appeared at 7–9 weeks. This occurrence was considerably earlier than the conventional implant devices in which the high alkaline phosphate levels usually appeared at the 12th week. This proves that the implant device according to the present invention is much more successful at promoting the formation of new bone mass than the prior art.

EXAMPLE 4

The dried material obtained in example 1 was calcined at 1100° C. for two hours in an electric furnace and crushed by a cage-type crusher. Thereafter, the dried material was screened by an ASTM standard screen to obtain a granular implant whose grain size was 250–500 μm. The granular implant material was provided with perfect spherical pores of 80 μm and micro pores of 0.3 μm. An adult beagle dog was subject to an artificial fracture of the femur under anesthesia. The marrow of this dog was filled with the granular implant and repositioned, sutured and fixed by a plaster cast. The plaster cast was removed at three days, seven days, and two weeks after the operation to obtain findings through X-ray images, respectively. The re-fixation by the plaster cast was carried out after each removal thereof. It was found three weeks later through an X-ray image that some new bone was being formed. Consequently, the fixation was released so that the dog was free to walk. Nevertheless, there were no defects, such as a re-fracture of the femur. It could be judged through the X-ray findings that the dog was completely cured after seven weeks had lapsed.

EXAMPLE 5

The implant element obtained by the calcination in example 4 was crushed by a cage-type crusher, and screened by ASTM standard screens of 140–7 meshes to classify groups of particles having particle sizes at intervals of 0.3 mm. Thereafter, the particle groups were mixed to obtain a granular implant for securing an artificial condyle.

Two adult beagle dogs (10 years old) were subject to the replacement of the condyles of the right and left rear legs with the artificial condyles to create a state of overload to thereby confirm efficiency of the implanted material. Namely, the femurs of the dogs were cut in the vicinity of vastus lat thereof, and thereafter, artificial condyles for middle size dogs produced by Richards Manufacturing Company (Tennessee, U.S.A.) were implanted. The cavities of the natural bone marrows were filled with the granular implant so as to immovably hold the stems of the artificial condyles.

After the operation, one of the dogs was subject only to an anti-infection treatment (NOBEKUTAN; trademark of Yoshitomi Pharamaceuticals K.K.) at the sutured portion and was kept in a fenced area for two weeks. The other dog's rear leg was immobilized with a plaster bandage for two weeks. After two weeks had lapsed, the dog was free to walk. There were no defects such as a space between the stem of the artificial condyles and the natural bone for either dog as identified through the use of X-rays even 20 weeks after the operation. Also, there was no loosening of the prosthetic. Furthermore, there were slight shadows in the form of clouds in the vicinity of the perfect spherical pores.

EXAMPLE 6

A granular implant of 0.1–0.5 mm was obtained by the same calcining and screening as those in the processes of example 4. It was confirmed that the particles contained the perfect spherical pores of 50 μm and micro pores of 0.3 μm.

A male mongrel dog suffering from a congenital malformation in which the spine was curved was subjected to a rachilysis by an external skeletal fixation to fill the defect portion with the granular implant. After the operation, findings through X-ray images were periodically obtained to determine the time at which the external skeletal fixation device could be removed. An image of a shadow in the form of clouds appeared in the vicinity of the particles one month after the operation, but this was considered to be the progression of new bone formation and adhesion to the natural bone. Accordingly, the fixation device was removed two months after the operation as it was considered safe. There were no abnormal findings such as a deformation or deterioration of the operated portion, even after one year had elapsed.

We claim:

1. A ceramic device providing an environment for promotion and formation of new bone, wherein said ceramic device is made of a sinter of calcium phosphate compound, containing a plurality of perfect spherical pores whose diameters are in a ranger of 10–450 μm to provide said environment for formation of a new bone, and a plurality of micro pores whose diameters are in a range 0.01–0.5 μm, which surround said perfect spherical pores to connect said perfect spherical pores with an outer surface of said ceramic device, wherein said micro pores interconnect with each other.

2. A ceramic device according to claim 1, wherein said ceramic device further comprises:

at least one pair of opposed surfaces; and at least one tubular passage of 0.6–1.2 mm diameter connecting said opposed surfaces.

3. A ceramic device according to claim 2, wherein a plurality of said tubular passages are provided so as to be spaced at a distance of 3–5 mm between each other in a cross section normal to a direction of said tubular passages.

4. A ceramic device according to claim 2, wherein said ceramic device is in a form of a rectangular shaped column, and wherein a first of said at least one tubular passage is provided at a center of said rectangular shaped column, and other said tubular passages are arranged around said center tubular passage in a hexagonally symmetrical manner.

5. A ceramic device according to claim 3, wherein said tubular passages include at least one central passage located at a center of a circle within said cross section normal to said direction of said tubular passages, and a plurality of peripheral passages located equidistantly from one another and from said central passage.

6. A ceramic device according to claim 5, wherein a diameter of said circle is substantially 1 cm, and said equi-distance is in a range of 3–5 mm.

* * * * *

UNITED STATES PATENT AND TRADEMARK OFFICE
CERTIFICATE OF CORRECTION

PATENT NO. : 5,531,794
DATED : July 2, 1996
INVENTOR(S) : S. TAKAGI et al.

It is certified that error appears in the above-indentified patent and that said Letters Patent is hereby corrected as shown below:

At column 10, line 1 (claim 1, line 5), change "ranger" to ---range---.

Signed and Sealed this

Eighteenth Day of February, 1997

Attest:

BRUCE LEHMAN

Attesting Officer

Commissioner of Patents and Trademarks